(12) United States Patent
Gorsek

(10) Patent No.: US 6,887,497 B2
(45) Date of Patent: May 3, 2005

(54) COMPOSITION FOR THE TREATMENT AND PREVENTION OF OSTEOARTHRITIS, RHEUMATOID ARTHRITIS AND IMPROVED JOINT FUNCTION

(75) Inventor: Wayne F. Gorsek, Boynton Beach, FL (US)

(73) Assignee: Vitacost.com, Inc., Boynton Beach, FL (US)

(*) Notice: Subject to any disclaimer, the term of this patent is extended or adjusted under 35 U.S.C. 154(b) by 0 days.

(21) Appl. No.: 10/322,586

(22) Filed: Dec. 19, 2002

(65) Prior Publication Data

US 2004/0121024 A1 Jun. 24, 2004

(51) Int. Cl.7 .............................................. A61K 35/78
(52) U.S. Cl. ...................................... 424/725; 424/776
(58) Field of Search .................................. 424/725, 766

(56) References Cited

U.S. PATENT DOCUMENTS

| | | | | |
|---|---|---|---|---|
| 4,680,289 A | * | 7/1987 | Applezweig | ................ 514/172 |
| 6,344,217 B1 | * | 2/2002 | Ruepp | ........................ 424/581 |
| 6,447,809 B1 | * | 9/2002 | Krumhar et al. | ............ 424/602 |
| 6,579,543 B1 | * | 6/2003 | McClung | ..................... 424/728 |
| 6,646,013 B1 | * | 11/2003 | Barker et al. | ................ 514/731 |
| 2002/0165169 A1 | * | 11/2002 | Kim et al. | ..................... 514/27 |
| 2003/0118672 A1 | * | 6/2003 | McPeak et al. | ............. 424/750 |

* cited by examiner

Primary Examiner—Patricia Leith
(74) Attorney, Agent, or Firm—Hoffman, Wasson & Gitler, PC

(57) ABSTRACT

The present invention involves a composition for oral ingestion that contains effective amounts of Glucosamine sulfate, Nettle Leaf, Quercetin, curcumin extract/curcuminoids, Selenium, Zinc, Vitamin C (calcium ascorbate) and Grape Seed Extract, as well as other ingredients and healthy filler ingredients. More specifically, this formulated product is a cartilage and joint maintenance and repair formulation. This formulation allows for enhanced function of joints and cartilage to treat and prevent osteoarthritis, rheumatoid arthritis and other joint ailments/diseases.

1 Claim, No Drawings

COMPOSITION FOR THE TREATMENT AND PREVENTION OF OSTEOARTHRITIS, RHEUMATOID ARTHRITIS AND IMPROVED JOINT FUNCTION

BACKGROUND OF THE INVENTION

The invention relates to a composition that contains the most potent combination of nutrients with clinical studies proven to assist in the treatment and prevention of osteoarthritis, rheumatoid arthritis, and improved joint function.

The advanced formulation is designed to promote healthy joints and cartilage as people age, which is critical to good health.

Emerging research confirms that nutrition may play a significant role in assisting the body to repair the damage to joints and cartilage. Glucosamine sulfate, along with specific antioxidant vitamins, minerals and phytonutrients, have been shown to actually reverse the progression of joint and cartilage deterioration. In addition to their effectiveness, all of these dietary supplements are extremely safe and free of dangerous side effects.

To ensure effective absorption and tissue utilization, it's highly recommended that one take Glucosamine in the sulfate form. This is the way Glucosamine is found in the body, and it lacks any known toxicity.

The best, the easiest and most cost-effective way to give your bones, joints, ligaments and cartilage the nutritional support they need is with a high-quality product that combines all the right supplements in the right dosages.

It is an objective of the present invention to provide a unique formulation, which allows individuals to improve, maintain and enhance joint function and cartilage.

SUMMARY OF THE INVENTION

The key to the unique formulation is a combination of specific vitamins, minerals, herbs and nutrients. These essential components in the amounts provided uniquely contribute to improved bone and cartilage strength.

The formulation contains effective amounts of Glucosamine sulfate, Nettle Leaf, Quercetin, Selenium (Selenomethionine), Zinc, Vitamin C(calcium or magnesium ascorbate or any mineral ascorbate) and Grape Seed Extract.

The formulation is preferably delivered in capsule form at four capsules per day.

DETAILED DESCRIPTION OF THE INVENTION

The present invention involves a composition for oral ingestion that contains effective amounts of Glucosamine sulfate, Nettle Leaf, Quercetin, Selenium (Selenomethionine), Zinc, Vitamin C (calcium or magnesium ascorbate) and Grape Seed Extract, as well as other ingredients and necessary filler ingredients. More specifically, this formulated product is a joint and cartilage maintenance and repair formulation. This formulation allows for enhanced function of joints and cartilages. As a result this formulation will be a effective and preventative and treatment for all forms of arthritis including osteoarthritis.

In order to secure the desired result the following essential components are provided:

Glucosamine sulfate is a naturally occurring substance in the body, synthesized in the chondrocytes. In failing joints this synthesis is defective and insufficient, and the supplementation with Glucosamine has proven to be beneficial. The body uses supplemented Glucosamine sulfate to synthesize the proteoglycans and the water-binding glycosaminoglycans (GAGs) in the cartilage matrix. In addition to providing raw material, the presence of Glucosamine sulfate seems to stimulate the chondrocytes in their production of these substances. Glucosamine sulfate also inhibits certain enzymes, which destroy the cartilage, e.g., collagenase and phospholipase. By blocking pathogenic mechanisms that lead to articular degeneration, Glucosamine sulfate improves joint function.

Nettle leaf is an herb that has a long tradition of use to benefit joint function. Nettle leaf extract has recently been found to contain a variety of active compounds, such as cyclooxygenase and lipoxygenase inhibitors. These two compounds cause pain and inflammation and reducing them has proven joint benefits.

Vitamin C in the calcium or magnesium or any mineral ascorbate form is a superior absorbed and retained form of Vitamin C with excellent benefits for joint function. Vitamin C is an essential building block for cartilage production; the degeneration of cartilage is the main cause of failing joints and arthritis as we age.

Grape seed extract, Quercetin, *Curcurma longa* (tumeric) is a rich source of beneficial phenolic compounds known as curcuminoids (tetrahydrocurcuminoids or curcumin extract) selenium and zinc (1-monomethionine) are a powerful combination of antioxidants that neutralize harmful free radicals. It is well proven free radicals cause oxidation and damage the body. These same free radicals can destroy your joints and cartilage. These combinations, forms and levels are unique and provide far greater protection from free radicals when compared to other single nutrients or formulations.

Additionally, the following is a breakdown of the preferred formulation:

Daily Dose (four capsules):

| | |
|---|---:|
| Vitamin C | 1,000 mg |
| (calcium ascorbate) | (100–20,000 mg) |
| Grape Seed Extract | 200 mg |
| | (20–4,000 mg) |
| Quercetin | 200 mg |
| | (20–4,000 mg) |
| Glucosamine Sulfate | 1,500 mg |
| | (100–7,000 mg) |
| Curcumin Extract/Curcuminoids | 350 mg |
| | (20 mg–8,000 mg) |
| Nettle Extract | 500 mg |
| | (50–10,000 mg) |
| Selenium (Selenomethione) | 200 mcg |
| | (20–8,000 mcg) |
| Zinc (1-monomethionine) | 15 mg |
| | (2–300 mg) |
| (Other ingredients: Silica, Cellulose, Magnesium Stearate, and Kosher Gelatin Capsule) | |

In addition to the key components, other components such as kosher gelatin (capsules), magnesium stearate and silica and cellulose are included to allow encapsulation and provide a effective delivery mechanism for the nutrients in this formulation. They are not part of the effective formulation.

Treating arthritis (cartilage and joint degeneration) is currently a frustrating effort. The current drugs only treat symptoms and do not repair the cartilage and joints. Many people suffer from progression and end up needing joint replacements. The formulation described safely and effective prevents and treats arthritis. Although the invention has been described primarily in connection with special and preferred embodiments, it will be understood that it is capable of modification without departing from the scope of the invention. The following claims are intended to cover all variations, uses, or adaptations of the invention, following, in general the principles thereof and including such departures from the present disclosure as come within known or customary practice in the field to which the invention pertains, or as are obvious to persons skilled in the field.

What is claimed is:

1. A composition for the treatment of osteoarthritis, rheumatoid arthritis, and to improve bone, ligament, cartilage and joint function comprising from:
   100 to 20,000 mg of calcium ascorbate;
   20 to 4,000 mg of grape seed extract;
   20 to 4,000 mg of Quercetin;
   35 to 7,000 mg of Glucosamine sulfate;
   50 to 10,000 mg of nettle extract;
   1.5 to 300 mg of zinc; and
   20 to 8,000 mcg of selenomethionine.

* * * * *